US008834373B2

(12) United States Patent
Fukukita et al.

(10) Patent No.: US 8,834,373 B2
(45) Date of Patent: Sep. 16, 2014

(54) ULTRASONOGRAPHIC DEVICE WITH WEIGHTED ADDITION OF DATA

(75) Inventors: Hiroshi Fukukita, Tokyo (JP); Hisashi Akiyama, Kanagawa (JP)

(73) Assignee: Konica Minolta, Inc., Tokyo (JP)

( * ) Notice: Subject to any disclaimer, the term of this patent is extended or adjusted under 35 U.S.C. 154(b) by 791 days.

(21) Appl. No.: 12/516,299

(22) PCT Filed: Nov. 21, 2007

(86) PCT No.: PCT/JP2007/072516

§ 371 (c)(1), (2), (4) Date: May 26, 2009

(87) PCT Pub. No.: WO2008/069021

PCT Pub. Date: Jun. 12, 2008

(65) Prior Publication Data

US 2010/0022890 A1 Jan. 28, 2010

(30) Foreign Application Priority Data

Dec. 1, 2006 (JP) ................................ 2006-326074

(51) Int. Cl.
*A61B 8/00* (2006.01)
*A61B 8/08* (2006.01)

(52) U.S. Cl.
CPC . *A61B 8/00* (2013.01); *A61B 8/463* (2013.01); *A61B 8/483* (2013.01)
USPC ............................ 600/443; 600/437; 600/459

(58) Field of Classification Search
USPC ............ 600/459, 437, 463, 472, 447; 73/606, 73/602, 596, 619, 625, 626
See application file for complete search history.

(56) References Cited

U.S. PATENT DOCUMENTS 5,438,994 A * 8/1995 Starosta et al. ............... 600/447
5,546,807 A 8/1996 Oxaal et al.
5,810,008 A * 9/1998 Dekel et al. .................. 600/443
5,842,473 A * 12/1998 Fenster et al. ............... 600/445

(Continued)

FOREIGN PATENT DOCUMENTS

JP 59118142 7/1984
JP 01-121040 A 5/1989

(Continued)

OTHER PUBLICATIONS

Machine translation of JP 2006/280768.*

(Continued)

*Primary Examiner* — Unsu Jung
*Assistant Examiner* — Rajeev Siripurapu
(74) *Attorney, Agent, or Firm* — Holtz, Holtz, Goodman & Chick PC

(57) ABSTRACT

A technique for an ultrasonographic device that can obtain respective rendering images for a plurality of regions of a 3D space is disclosed. According to the technique, a transmission beam former generates an ultrasonic beam for scanning a plurality of regions of interest and drives a matrix array. When a reception beam former generates a plurality of beam forming signals, respectively corresponding to the regions of interest, in accordance with reception signals of the matrix array generated by reflection wave from the respective regions of interest, a signal processing unit processes the beam forming signals and, with a viewpoint set for each of the regions of interest as a standard, generates respective rendering images of the plurality of regions of interest. A display unit displays the rendering images in parallel. A control unit carries out setting of the plurality of regions of interest and the viewpoints, by an external operation.

14 Claims, 4 Drawing Sheets

(56) References Cited

U.S. PATENT DOCUMENTS

| | | | | |
|---|---|---|---|---|
| 6,471,652 | B2 * | 10/2002 | Fraser et al. | 600/459 |
| 2003/0013955 | A1 * | 1/2003 | Poland | 600/437 |
| 2004/0215077 | A1 * | 10/2004 | Witt et al. | 600/443 |

FOREIGN PATENT DOCUMENTS

| | | | |
|---|---|---|---|
| JP | 2001-515373 | A | 9/2001 |
| JP | 2004-530502 | A | 10/2004 |
| JP | 2006-280768 | A | 10/2006 |
| WO | 03-001240 | A1 | 1/2003 |

OTHER PUBLICATIONS

International Search Report for PCT/JP2007/072516 dated Feb. 26, 2008.

* cited by examiner 2
20
1
5
P1
L1
3
4
14
V2
12
11
L2
P2
V1
13
W2
6
W1
7

A1
P1
L1
6
8
D1
D2
D3
D4
X
R1
R2
R3
R4
W1

ULTRASONOGRAPHIC DEVICE WITH WEIGHTED ADDITION OF DATA

TECHNICAL FIELD

Present invention relates to an ultrasonographic device for displaying 3D (three-dimensional) data.

BACKGROUND ART

The ultrasonic data in the ultrasonographic device is usually obtained as a frame, and each frame corresponds to the sweep of the ultrasonic beam emitted from a transducer surface. The sweep of the ultrasonic beam is typically obtained by generating a plurality of scanning lines along one scanning surface. The set of the scanning lines typically forms one referred to as "Slice". The slice typically corresponds to one frame. For example, in a 3D (volume) scanning, the many slices configure the frame.

As for a two-dimensional (2D) matrix probe, a 3D shape is formed as the set of the many slices (frames). Those many slices generate the ultrasonic data for a volume occupied by the slices. When all of the data gathered for a given volume are processed, a calculation load becomes great, which reduces the frame rate of the gathered data. So, a demand for realizing a system that displays a 3D data without requiring the processing of all the data was eager.

As a device for satisfying the demand, an ultrasonographic device that includes: a 2D matrix probe; a system control device for determining at least two ultrasonic slices that correspond to a desirable ultrasonic image; a scanning converter for obtaining the desirable ultrasonic image from the data obtained from at least two ultrasonic slices; and a display for displaying the desirable ultrasonic image is proposed (for example, refer to the following patent document 1).

Patent Document 1: PCT-Based Japanese Patent Application Publication 2004-530502 (Paragraph 0016 to 0032)

However, the above-mentioned conventional ultrasonographic device had a problem that the desirable ultrasonic image could be obtained as only the slice.

DISCLOSURE OF THE INVENTION

The present invention is proposed to solve the above-mentioned problems, and its object is to provide the ultrasonographic device that can obtain a rendering image for each of a plurality of regions of interest of a 3D space.

In order to attain the above-mentioned object, the ultrasonographic device according to the present invention has a matrix array in which ultrasonic transducers are arranged at least two-dimensionally; a transmission beam former for driving the matrix array so as to generate an ultrasonic beam for scanning a plurality of regions of interest of a preset 3D space; a reception beam former for generating a plurality of beam forming signals that correspond to the regions of interest, respectively, in accordance with the reception signal of the matrix array by the reflection waves from the plurality of regions of interest; a signal processing unit for processing the beam forming signals generated by the reception beam former and consequently generating each rendering image of the plurality of regions of interest, with a viewpoint preset for each of the regions of interest as a standard; a display unit for displaying in parallel the plurality of rendering images generated by the signal processing unit; means for setting the plurality of regions of interest to be scanned by the transmission beam former, by an external operation; and means for setting the viewpoint at which the signal processing unit generates the rendering image, for each of the regions of interest, and by using the transmission beam former, it is possible to carry out the scanning faster than the scanning of the entire 3D space.

With this configuration, it is possible to obtain the rendering image of the volume for each of the plurality of regions of interest of the 3D space.

Also, in the ultrasonographic device according to the present invention, the control unit has means for selecting a longitudinal cross-section for each of the regions of interest by the external operation, and setting at least one viewpoint, on a normal of each of the selected longitudinal cross-sections.

With this configuration, it becomes easy to set the viewpoints when the rendering images of the volumes are obtained for the plurality of regions of interest of the 3D space.

Also, in the ultrasonographic device according to the present invention, the control unit has means for setting test depths of the plurality of regions of interest, independently of each other, by the external operation.

With this configuration, it is possible to set the scanning speed of the ultrasonic beam on the basis of each of the test depths for the plurality of regions of interest of the 3D space. Thus, it is possible to carry out the fast scanning.

Also, in the ultrasonographic device according to the present invention, the control unit has means for setting the volume rates at which the plurality of regions of interest are scanned, independently of each other, by the external operation.

With this configuration, among the plurality of regions of interest, as for the region of interest whose target degree is higher or the region of interest whose motion is quicker, it is possible to set the volume rate of the scanning higher than the other regions of interest. Thus, the beneficial diagnostic information is obtained.

Also, in the ultrasonographic device according to the present invention, the control unit has means that can change each of the scanning speeds of the plurality of regions of interest, within one cardiac beat, by the external operation.

With this configuration, within one cardiac beat, when in the plurality of regions of interest, the peak value of the displacement speeds in their organizations is different for each of the regions of interest, the scanning speed of the ultrasonic beam is controlled to become high on the basis of the peak value of each of the displacement speeds. Thus, the beneficial diagnostic information is obtained.

Also, in the ultrasonographic device according to the present invention, the control unit has means for dividing the plurality of regions of interest into respectively partial regions, by the external operation, and setting a scanning order of the partial regions in the region of interest so that the differential partial portions in the differential regions of interest are sequentially scanned, with at least one of the partial regions as a scanning unit.

With this configuration, the plurality of regions of interest are scanned in parallel, thereby obtaining the beneficial diagnostic information.

Also, in the ultrasonographic device according to the present invention, the scanning of the plurality of regions of interest is synchronous with the cardiac beat.

With this configuration, it is possible to change the volume rates of the plurality of regions of interest at the timing specified for the cardiac beat.

The present invention can provide the ultrasonographic device having an effect in which the plurality of regions of interest of the 3D space are scanned by the ultrasonic beam, and the viewpoint is independently set for each scanning region, and the plurality of images obtained by the rendering are displayed in parallel, and consequently the rendering images of the volumes for the plurality of regions of interest of the 3D space can be obtained, thereby enabling the fast scanning as compared with the case of obtaining the image of the entire 3D space.

BEST MODE FOR CARRYING OUT THE INVENTION

The present invention will be described below in detail in accordance with the preferable embodiments shown on the drawings.

<First Embodiment>

Figure 1A:
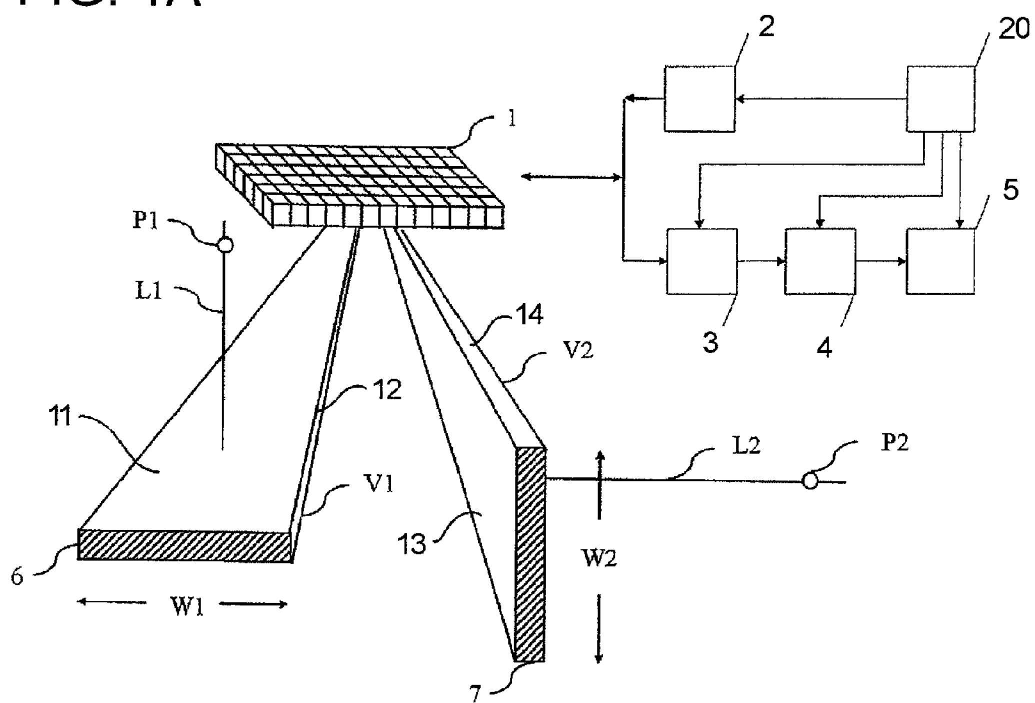
FIG. 1A is a view showing a state of scanning by an ultrasonic beam, together with a block diagram showing a configuration of a first embodiment of the ultrasonographic device according to the present invention.
Figure 1B:
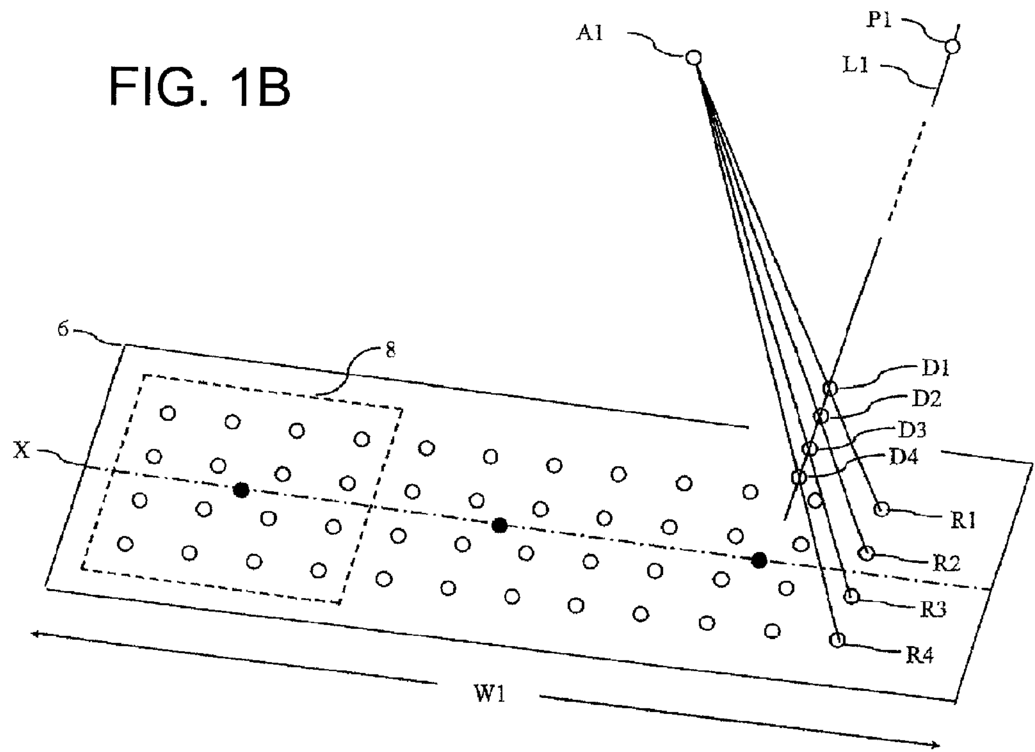
FIG. 1B is a view showing a situation in which a bottom surface of a scanning region in the first embodiment interests with the ultrasonic beam.
Figure 1C:
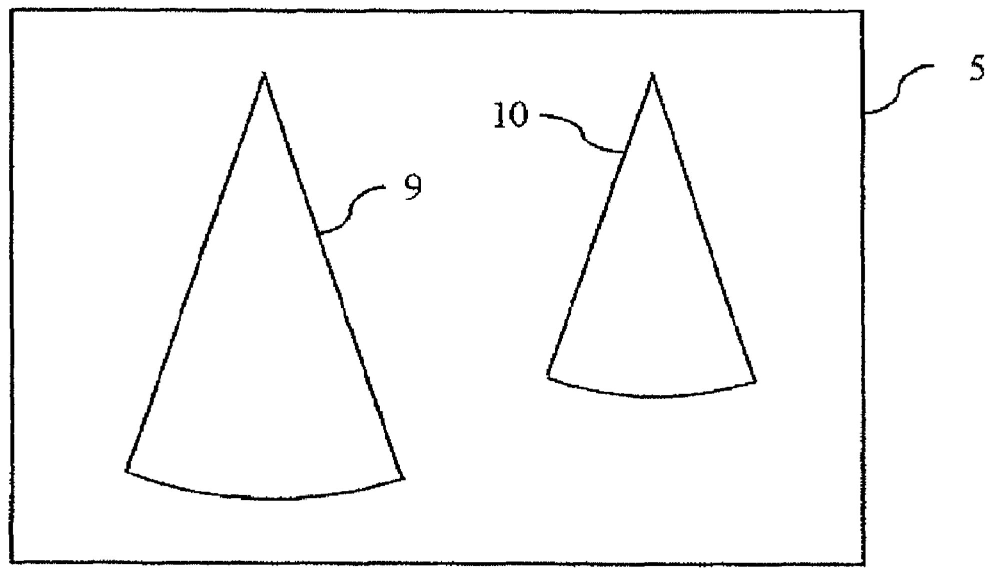
FIG. 1C is a view showing a displaying example of an image in the first embodiment.

FIG. 1A is the view showing the state of scanning by the ultrasonic beam, together with the block diagram showing the configuration of the first embodiment of the ultrasonographic device according to the present invention, FIG. 1B is the view showing the situation in which the bottom surface of the scanning region in the first embodiment and the ultrasonic beam intersect, and FIG. 1C is the view showing the displaying example of the image in the first embodiment.

In FIG. 1A, a matrix array 1 is composed of many ultrasonic transducers which are two-dimensionally arrayed, and they are combined with acoustic parts (not shown), respectively, and mounted inside a housing so that the ultrasonic probe is formed. A transmission beam former 2 drives the matrix array 1 so as to generate the ultrasonic beam for scanning the regions of interest of the preset 3D space. The transmitted ultrasonic beam is reflected inside the test body, and its reflection wave is received by the matrix array 1. A reception beam former 3 carries out a process for amplifying and delaying the signal received by the matrix array 1 and generates the plurality of beam forming signals corresponding to the regions of interest. A signal processing unit 4 processes the beam forming signal generated by the reception beam former 3 and consequently generates the rendering image of the region of interest, with the preset viewpoint as the standard. A display unit 5 displays the rendering image generated by the signal processing unit 4. A control unit 20 correlates and controls the transmission beam former 2, the reception beam former 3 and the signal processing unit 4, in accordance with the external operation.

Among them, the control unit 20 has: a function for setting the plurality of regions of interest scanned by the transmission beam former 2 by using the known input devices such as a keyboard, a touch panel and the like; a function for setting the viewpoint at which the signal processing unit 4 generates the rendering image, for each of the regions of interest; and a function for displaying the plurality of rendering images generated by the signal processing unit 4, in parallel, on the display unit 5.

The operation of the first embodiment as configured above will be described below. Through the input device (not shown) contained in the control unit 20, a user sets the plurality of regions of interest and the viewpoint for each of the regions of interest. The setting of this viewpoint is carried out by selecting the longitudinal cross-section where the region of interest is scanned and then setting at least one viewpoint on the normal of the selected longitudinal cross-section. In response to the setting of the control unit 20, in the matrix array 1, as shown in FIG. 1A, the ultrasonic beam is used to three-dimensionally scan a region V1 and a region V2, which are the regions of interest of the 3D space. The region V1 creates a pyramidal form, which has an apex (not shown) inside the matrix array 1 and is represented by: a rectangular bottom surface 6 indicated by oblique lines; two sides 11 that pass through the long sides and apex of the bottom surface 6; and two sides 12 that pass through the short sides and apex of the bottom surface 6, and the length of the long side of the bottom surface 6 is W1. Then, a viewpoint P1 is set on the extension line of one normal L1 for the later-described longitudinal cross-section in the middle between the two sides 11. Similarly, the region V2 creates a pyramidal form, which has an apex (not shown) inside the matrix array 1 and is represented by: a rectangular bottom surface 7 indicated by oblique lines; two sides 13 that pass through the long sides and apex of the bottom surface 7; and two sides 14 that pass through the short sides and apex of the bottom surface 7, and the length of the long side of the bottom surface 7 is W2. Then, a viewpoint P2 is set on the extension line of one normal L2 for the later-described longitudinal cross-section in the middle between the two sides 13.

In FIG. 1B, on a surface 8 surrounded with a dashed line on the bottom surface 6 of the region V1, an intersection position between the bottom surface 6 and one transmission beam is indicated by a black circle, and intersection positions between the bottom surface 6 and 16 (=4×4) parallel reception beams obtained from the ultrasonic beam of one transmission are indicated by white circles. Similarly, with the transmission of the plurality of transmission beams, the positions at which the two-dimensionally arrayed parallel reception beams intersect are indicated on the bottom surface 6. Also, each of the reception beams intersects at an apex A1, and the reception beams, which pass through the apex A1 and the respective sides of the bottom surface 6, form the region V1. In this example, the region V1 is composed of four slices. The longitudinal cross-section (not shown) of the centers of one pair of sides 11 in the region V1 intersects the bottom surface 6 on an alternate long and short dash line X and vertically intersects the normal L1. The alternate long and short dash line X is selected so as to be approximately parallel to the longitudinal direction of the bottom surface 6.

Here, the signal processing unit 4 carries out the following process. When the viewpoint P1 on the normal L1 shown in FIG. 1 is infinitely remotely located, an weighting addition (including the addition of a voxel value and the definition of an opacity) is performed on each of image data D1, D2, D3 and D4, which are located on the same line when they are viewed from the viewpoint P1, among the image data obtained by the reception beams corresponding to positions R1, R2, R3 and R4 at which the bottom surface 6 and the reception beams intersect. The weighting addition is carried out at the various depths of the reception beams. Since the similar operation is performed on each of the reception beams, the rendering of the volume is completed for the region v1, and the 3D image is consequently obtained. Similarly, the 3D image is obtained for the region V2. So, on the display unit 5, as shown in FIG. 1C, a 3D image 9 of the region V1 and a 3D image 10 of the region V2 are displayed in parallel.

In this way, according to the first embodiment of the ultrasonographic device according to the present invention, the plurality of regions of the 3D space are scanned by the ultrasonic beam, and the viewpoint is independently set for each of the scanning regions, and the plurality of images obtained by the rendering are displayed in parallel. Thus, it is possible to obtain the rendering images of the volumes for the plurality of regions of interest of the 3D space, and it is possible to carry out the fast scanning as compared with the case of obtaining the image of the entire 3D space. Also, since the viewpoint of each of the scanning regions is located on the normal of the longitudinal cross-section in each of the scanning regions, the position setting of the viewpoint is easy.

By the way, FIG. 1B shows the case in which the number of the transmission ultrasonic beams is 1 in the direction orthogonal to the bottom surface 6. However, even when the number is 2 or more, the similar effect is obtained.

<Second Embodiment>

Figure 2A:
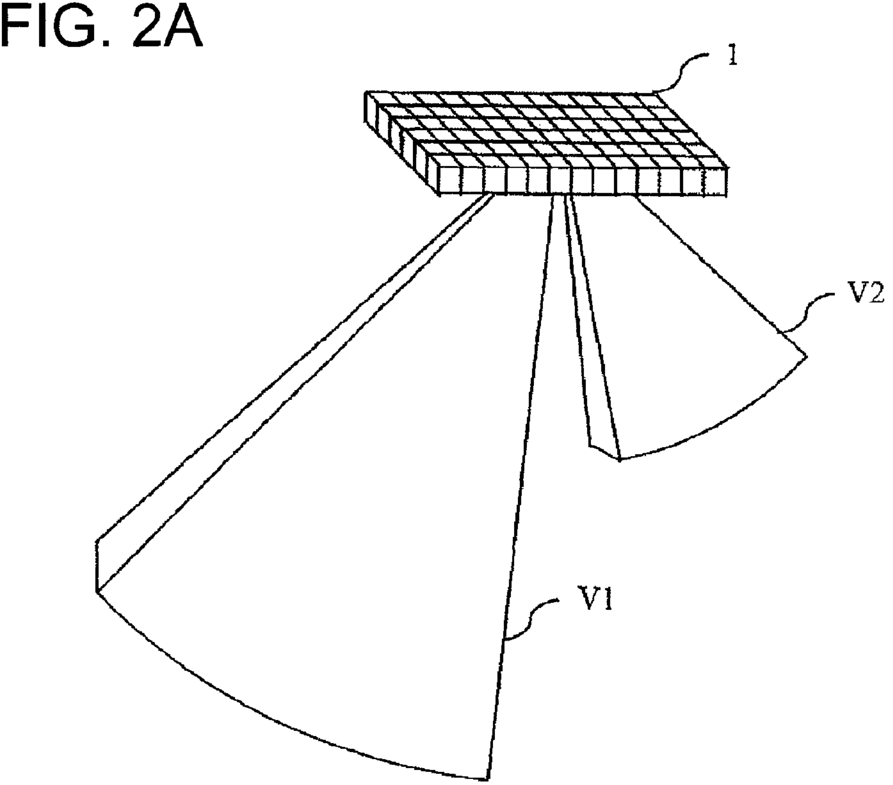
FIG. 2A is a view showing a state of scanning by an ultrasonic beam in a second embodiment of the ultrasonographic device according to the present invention.
Figure 2B:
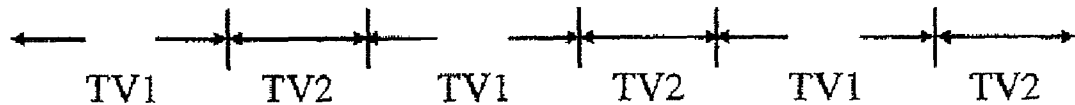
FIG. 2B is a view showing timings when a plurality of regions are scanned, according to the second embodiment.

FIG. 2A is the view showing the state of scanning by the ultrasonic beam in the second embodiment of the ultrasonographic device according to the present invention, and FIG. 2B is the view showing the timings when the plurality of regions are scanned according to the second embodiment. By the way, the hardware configurations of the matrix array 1, the transmission beam former 2, the reception beam former 3, the signal processing unit 4, the display unit 5 and the control unit 20 are equal to the first embodiment shown in FIG. 1A. Thus, their illustrations and descriptions are omitted.

In the second embodiment, the means for setting the test depths of the plurality of regions of interest, independently of each other, by the external operation, is installed in the control unit 20. That is, as shown in FIG. 2A, when in the matrix array 1, the region V1 and the region V2 are three-dimensionally scanned, in such a way that the test depth of the region V1 and the test depth of the region V2 differ from each other, they can be set independently of each other.

Next, as for the operation of the second embodiment, the portion whose configuration differs from the first embodiment is described. At first, the region V1 is scanned at a scanning time TV1. Next, the region V2 is scanned at a scanning time TV2 (<TV1). Such a scanning is alternately performed as shown in FIG. 2B. At this time, since the region V2 is shallower in test depth than the region V1, the reception time is short. As a result, the entire scanning time becomes short, and the scanning speed becomes fast. Hence, this is suitable for the 3D displaying of the organization that moves at a high speed.

In this way, according to the second embodiment of the ultrasonographic device according to the present invention, the test depths of the plurality of regions can be independently set. Thus, it is possible to set the scanning speeds of the ultrasonic beams, on the basis of the respective test depths for the plurality of regions of interest of the 3D space, and it is possible to carry out the fast scanning.

>Third Embodiment≤

Figure 3A:
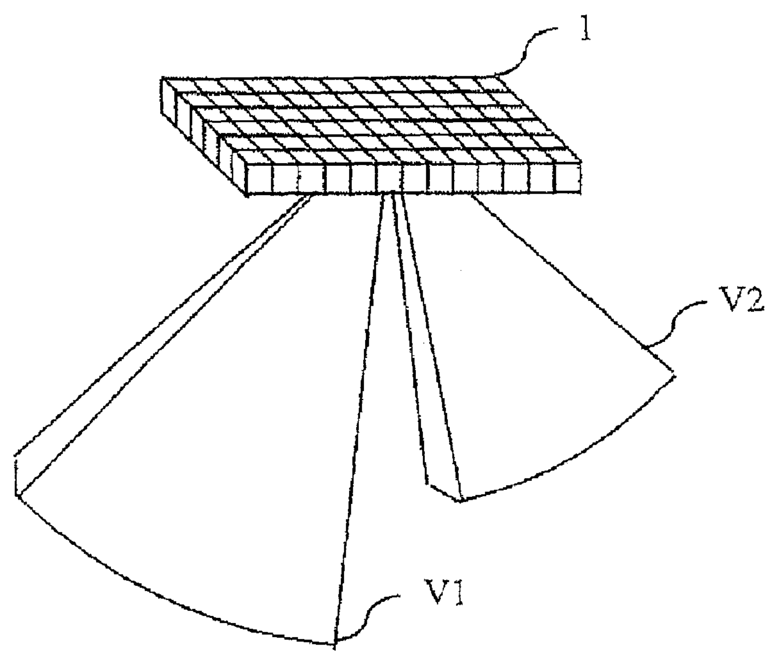
FIG. 3A is a view showing a state of scanning by an ultrasonic beam in a third embodiment of the ultrasonographic device according to the present invention.
Figure 3B:
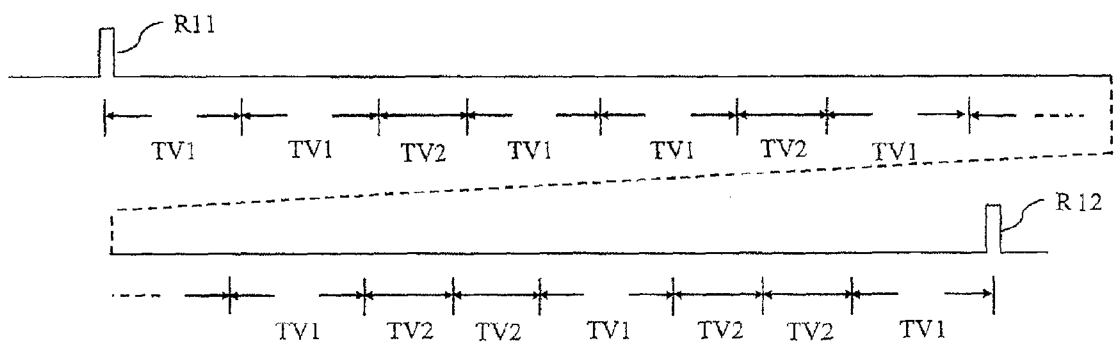
FIG. 3B is a view showing timings when a plurality of regions are scanned, according to the third embodiment.

FIG. 3A is the view showing the state of scanning by the ultrasonic beam of the third embodiment of the ultrasonographic device according to the present invention, and FIG. 3B is the view showing the timings when the plurality of regions are scanned according to the third embodiment. By the way, the hardware configurations of the matrix array 1, the transmission beam former 2, the reception beam former 3, the signal processing unit 4, the display unit 5 and the control unit 20 are equal to the first embodiment shown in FIG. 1A. Thus, their illustrations and descriptions are omitted.

In the third embodiment, the means for setting the volume rates at which the plurality of regions of interest are scanned, independently of each other, by the external operation, and the means for enabling the scanning speeds of the plurality of regions of interest to be changed within one cardiac beat, respectively, are installed in the control unit 20.

Next, as for the operation of the third embodiment, the portion whose configuration differs from the first embodiment is described. As shown in FIG. 3A, in the matrix array 1, the region V1 and the region V2 are three-dimensionally scanned. At the time of this 3D scanning, a plurality of pulses R11, R12 synchronous with the cardiac beat can be obtained from a living body. As the pulses R11, R12, for example, an R-wave trigger obtained from a cardiac waveform may be used. Then, immediately after the pulse R11, the region V1 is scanned two times at the scanning time TV1. Then, the region V2 is scanned one time at the scanning time TV2 (<TV1). Thus, immediately after the pulse R11, the volume rate of the region V1 can be made higher than the volume rate of the region V2. On the other hand, immediately before the pulse R12, the region V1 is scanned one time at the scanning time TV1. Next, the region V2 is scanned two times at the scanning time TV2. Hence, immediately before the pulse R12, the volume rate at which the region V2 is scanned can be made higher than the volume rate at which the region V1 is scanned.

In this way, according to the third embodiment of the ultrasonographic device according to the present invention, the volume rates at which the plurality of regions are scanned by the ultrasonic beam can be independently set, thereby enabling the volume rates of the plurality of regions to be varied at the particular timing of the cardiac beat. For example, such as a mitral valve of a heart and an aortic valve, when the portions whose closing timings are different are observed, it is possible to increase the volume rates at which the respective regions are scanned at the timings when the respective valves are closed.

<Fourth Embodiment>

Figure 4A:
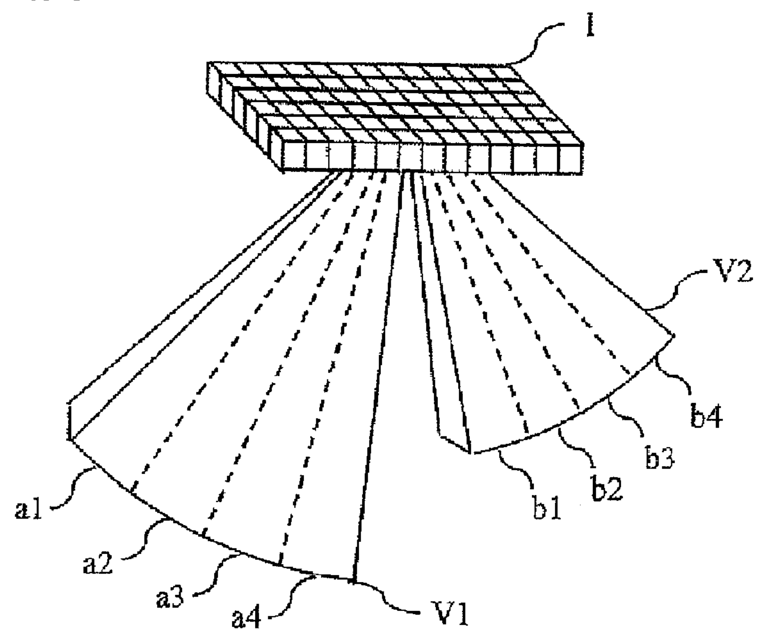
FIG. 4A is a view showing a state by scanned by an ultrasonic beam in a fourth embodiment of the ultrasonographic device according to the present invention.
Figure 4B:
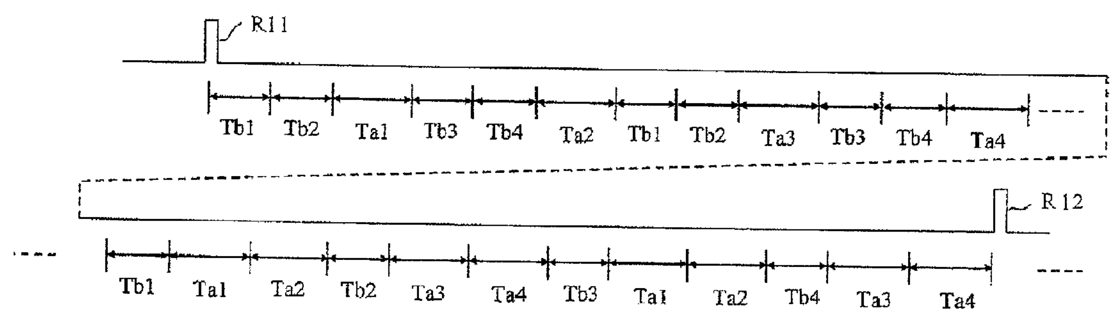
FIG. 4B is a view showing timings when a plurality of regions are scanned, according to the fourth embodiment.

FIG. 4A is the view showing the state of scanning by the ultrasonic beam of the fourth embodiment of the ultrasonographic device according to the present invention, and FIG. 4B is the view showing the timings when the plurality of regions are scanned according to the third embodiment. By the way, the hardware configurations of the matrix array 1, the transmission beam former 2, the reception beam former 3, the signal processing unit 4, the display unit 5 and the control unit 20 are equal to the first embodiment shown in FIG. 1A. Thus, their illustrations and descriptions are omitted.

In the fourth embodiment, the means for dividing the plurality of regions of interest into the partial regions, respectively, by the external operation, and the means in which with at least one partial region as one scanning unit, in such a way that the differential partial regions in the differential regions of interest are sequentially scanned, the scanning order of the partial regions in the region of interest is set are installed in the control unit 20.

The detailed operation of the fourth embodiment will be described below. As shown in FIG. 4A, in the matrix array 1, the region V1 and the region V2 are three-dimensionally scanned. The region V1 is divided into partial regions a1, a2, a3 and a4. The region V2 is divided into partial regions b1, b2, b3 and b4. When those partial regions are three-dimensionally scanned, pulses R11, R12 synchronous with the cardiac beat are obtained from the living body. As the pulses R11, R12, for example, an R-wave trigger obtained from the cardiac waveform may be used.

So, immediately after the pulse R11, the partial region b1 is scanned at the scanning time Tb1, and the partial region b2 is scanned at the scanning time Tb2 (=Tb1). Next, the partial region a1 is scanned at the scanning time Ta1 (>Tb1). Moreover, the partial region b3 is scanned at the scanning time Tb3 (=Tb1), and the partial region b4 is scanned at the scanning time Tb4 (=Tb1). Next, the partial region a2 is scanned at the scanning time Ta2 (=Ta1). In this way, the scanning of the volume of the region V2 is completed. Moreover, the partial region b1 is scanned at the scanning time Tb1, and the partial region b2 is scanned at the scanning time Tb2. Next, the partial region a3 is scanned at the scanning time Ta3 (=Ta1). Moreover, the partial region b3 is scanned at the scanning time Tb3, and the partial region b4 is scanned at the scanning time Tb4. Next, the partial region a4 is scanned at the scanning time Ta4 (=Ta1). In this way, the scannings of the volumes of the region V1 and the region V2 are completed. As mentioned above, immediately after the pulse R11, the volume rate of the scanning of the region V2 can be made higher than the volume rate of the scanning of the region v1.

On the other hand, immediately before the pulse R12, the partial region b1 is scanned at the scanning time Tb1. In succession, the partial regional is scanned at the scanning time Ta1, and the partial region a2 is scanned at the scanning time Ta2. Next, the partial region b2 is scanned at the scanning time Tb2. Moreover, the partial region a3 is scanned at the scanning time Ta3, and the partial region a4 is scanned at the scanning time Ta4. Next, the partial region b3 is scanned at the scanning time Tb3. Moreover, the partial region a1 is scanned at the scanning time Ta1, and the partial region a2 is scanned at the scanning time Ta2. Next, the partial region b4 is scanned at the scanning time Tb4. Moreover, the partial region a3 is scanned at the scanning time Ta3, and the partial region a4 is scanned at the scanning time Ta4. In this way, the scannings of the volumes of the region V1 and the region V2 are completed. As mentioned above, immediately before the pulse R12, the volume rate of the scanning of the region V1 can be made higher than the volume rate of the scanning of the region V2.

As mentioned above, the fourth embodiment of the ultrasonographic device according to the present invention is designed such that the plurality of regions are divided into the partial regions, respectively, and the plurality of regions are alternately scanned, and the scanning speeds of the divided partial regions are changed, respectively, and the volume rates at which the plurality of regions are scanned by the ultrasonic beams can be independently set, which enables the plurality of regions to be scanned in parallel and enables the volume rates of the plurality of scanning regions to be changed at the particular timing of the cardiac beat.

By the way, in the above-mentioned respective embodiments, the case of using the ultrasonic probe configured as the matrix array in which the ultrasonic transducers are two-dimensionally arrayed is described. However, in a case that the 3D scanning is possible, even if the different ultrasonic probe is used, the operation similar to the above-mentioned description can be carried out.

Also, in the above-mentioned respective embodiments, the case in which the number of the regions of interest is 2 is described. However, even in a case that the number of the regions of interest is 3 or more, the operation similar to the above-mentioned description can be carried out.

Industrial Applicability

As mentioned above, the ultrasonographic device according to the present invention has the effect that the rendering image of the volume can be obtained for each of the plurality of regions of interest of the 3D space and that the fast scanning become possible as compared with the case of obtaining the image of the entire 3D space, because the plurality of regions of the 3D space are scanned by the ultrasonic beam, and the viewpoints are independently set for the respective scanning regions, and the plurality of images obtained by the rendering are displayed in parallel, and this is useful for the ultrasonographic device and the like in which the rendering image is obtained for each of the plurality of regions of the 3D space.

The invention claimed is:

1. An ultrasonographic device comprising:

a matrix array in which ultrasonic transducers are arrayed at least two-dimensionally;

a transmission beam former configured to drive said matrix array so as to generate an ultrasonic beam to scan a plurality of regions of interest of a preset 3D space;

a reception beam former configured to generate a plurality of beam forming signals corresponding to respective regions of interest, of the plurality of regions of interest, in accordance with reception signals of said matrix array generated from reflection waves received from said plurality of regions of interest;

a signal processing unit configured to process the plurality of beam forming signals generated by said reception beam former and to consequently generate respective rendering images of said plurality of regions of interest, with respective viewpoints set for each of said plurality of regions of interest as a standard to generate the respective rendering images;

a display unit configured to display the respective rendering images generated by said signal processing unit, in parallel; and a control unit configured to set said plurality of regions of interest scanned by said transmission beam former, and said view points from which said signal processing unit generates the respective rendering images for each of said plurality of regions of interest in accordance with user input, wherein the control unit, to set the viewpoints, is further configured to select respective longitudinal cross-sections for each of the plurality of regions of interest in accordance with the user input and to set at least one viewpoint on a normal of each longitudinal cross-section selected, said signal processing unit is further configured to perform weighted addition on image data inside one of the regions of interest, wherein the weighted addition is performed respectively for sets of pieces of image data, the sets being located respectively on a plurality of straight lines, extending from the same viewpoint set on the normal of the selected longitudinal cross-section of the region of interest and through the region of interest, to generate a rendering image corresponding to the region of interest as viewed from the viewpoint, based on the sets of pieces of image data on which the weighted addition has been respectively performed, wherein with said transmission beam former, it is possible to carry out a scanning faster than a case of scanning the whole of said 3D space.

2. The ultrasonographic device according to claim 1, wherein said control unit is further configured to set respective depths from the matrix array to respective regions of interest of said plurality of regions of interest which are respectively scanned, independently of each other, in accordance with the user input.

3. The ultrasonographic device according to claim 1, wherein said control unit is further configured to set respective volume rates at which said plurality of regions of interest are scanned, independently of each other, in accordance with the user input.

4. The ultrasonographic device according to claim 1, wherein said control unit is further configured to change respective scanning speeds of said plurality of regions of interest within one cardiac beat in accordance with the user input.

5. The ultrasonographic device according to claim 1, wherein said control unit is further configured to divide said plurality of regions of interest into respective partial regions in accordance with the user input to define at least one of said respective partial regions as a scanning unit, and to set a scanning order of the respective partial regions in respective regions of interest so that differential partial regions in differential regions of interest are sequentially scanned.

6. The ultrasonographic device according to claim 1, wherein the transmission beam former synchronizes scans of said plurality of regions of interest with a cardiac beat.

7. The ultrasonographic device according to claim 1, wherein the pieces of image data in each set on which the weighted addition is performed are respectively located at corresponding positions of respective reception signals intersecting the corresponding straight line on which the pieces of image data in each set are located, and the weighted addition is performed for each set based on respective depths of the corresponding positions of the respective reception signals from the viewpoint.

8. A method for an ultrasonographic device, comprising:

setting a plurality of regions of interest of a three-dimensional space, respective longitudinal cross-sections of respective regions of interest of the plurality of regions of interest, and respective viewpoints on respective normals of the respective longitudinal cross-sections, in accordance with user input;

driving a matrix array having ultrasonic transducers arrayed two-dimensionally to generate an ultrasonic beam for scanning the plurality of regions of interest of the three-dimensional space;

generating a plurality of beam forming signals corresponding to respective regions of interest, of the plurality of regions of interest, based on receptions signals generated by the matrix array from reflection waves received from the plurality of regions of interest;

generating respective rendering images, based on the plurality of beam forming signals and the respective viewpoints set for respective regions of interest of the plurality of regions of interest, respectively corresponding to the plurality of regions of interest, wherein generating the respective rendering images comprises performing a weighted addition on image data inside one of the regions of interest, wherein the weighted addition is performed respectively for sets of pieces of image data, the sets being located respectively on a plurality of straight lines, extending from the same viewpoint set on the normal of the set longitudinal cross-section of the region of interest and through the region of interest, to generate a rendering image corresponding to the region of interest as viewed from the viewpoint based on the on the sets of pieces of image data on which the weighted addition has been respectively performed; and displaying, in parallel, the respective rendering images generated.

9. The method according to claim 8, wherein the pieces of image data in each set on which the weighted addition is performed are respectively located at corresponding positions of respective reception signals intersecting the corresponding straight line on which the pieces of image data in each set are located, and the weighted addition is performed for each set based on respective depths of the corresponding positions of the respective reception signals from the viewpoint.

10. The method according to claim 8, further comprising setting respective test depths of the plurality of regions of interest, independently of each other, in accordance with the user input.

11. The method according to claim 8, further comprising setting respective volume rates at which the plurality of regions of interest are scanned, independently of each other, in accordance with the user input.

12. The method according to claim 8, further comprising changing respective scanning speeds of the plurality of regions of interest within one cardiac beat in accordance with the user input.

13. The method according to claim 8, further comprising dividing the plurality of regions of interest into respective partial regions in accordance with the user input, defining at least one of the respective partial regions as a scanning unit, and setting a scanning order of the respective partial regions in respective regions of interest so that differential partial regions in differential regions of interest are sequentially scanned.

14. The method according to claim 8, further comprising synchronizing scans of the plurality of regions of interest with a cardiac beat.

* * * * *